United States Patent
Shubin, Sr.

[11] Patent Number: 5,806,523
[45] Date of Patent: Sep. 15, 1998

[54] PROPHYLACTIC AND PROSTHETIC DEVICE

[76] Inventor: Steven A. Shubin, Sr., 801 N. Weston La., Austin, Tex. 78733

[21] Appl. No.: 866,448

[22] Filed: May 30, 1997

[51] Int. Cl.$^6$ ........................................................ A61F 6/02
[52] U.S. Cl. .......................... 128/842; 128/844; 128/918; 600/38
[58] Field of Search ..................................... 128/842, 844, 128/918; 600/38–39; 604/347–353

[56] References Cited

U.S. PATENT DOCUMENTS

| | | | |
|---|---|---|---|
| 2,471,360 | 5/1949 | Thorne | 600/39 |
| 2,899,957 | 8/1959 | Briggs | 600/39 |
| 4,369,284 | 1/1983 | Chen . | |

*Primary Examiner*—Michael A. Brown
*Attorney, Agent, or Firm*—John S. Munday; Stephen G. Stanton

[57] ABSTRACT

A prophylactic and prosthetic device comprising an elastomeric gel formed into a tubular shape generally replicating that of the human male sex organ or member. The exterior of the device may be molded or otherwise formed to have the appearance of the member, or it may have a generally cylindrical shape such as that of conventional condoms. The texture of the exterior simulates the color, physical properties and tactile feel of human flesh, and, when wet with water soluble fluids, has relatively low friction similar to the human skin that it replicates. The interior of the device is hollow, providing space for insertion of the human male sex member in an aroused state. The texture of the interior surface is highly tacky so that it virtually sticks to the skin of the male user. The preferred elastomeric gel is formed from a mixture of plasticizing oil and a block copolymer selected from SEBS block copolymers, SEPS block copolymers and mixtures thereof. The most preferred gel is formed from a mixture of plasticizing oil and an admixture of SEBS copolymers and SEPS block copolymers in a polymer ratio of 1:5 to 5:1, with 1:1 being most preferred. The preferred elastomeric gel is formed from a mixture of 5–15% by weight of the block copolymer and 85–95% by weight of the plasticizing oil, and trace amounts of pigments and fillers.

14 Claims, 1 Drawing Sheet

PROPHYLACTIC AND PROSTHETIC DEVICE

FIELD OF THE INVENTION

The present invention relates to a prophylactic device such as a condom. More particularly the present invention relates to a prophylactic device that may also be used as a male sex organ size enhancing device.

BACKGROUND OF THE INVENTION

Over the years since synthetic materials such as latex and elastomers have been developed, efforts have been made to use such materials in birth control and disease prevention devices, generally known as prophylactics or condoms. In addition, these materials and others have been used to replicate the male sex organ, as a prosthesis or to assist in enhancing the size thereof.

Chen U.S. Pat. No. 4,640,270 and McAllister U.S. Pat. No. 5,127,396 are examples of devices that are used substantially for prosthetic benefits. Both require straps, a base, and various mechanical components, and are not effective in providing a natural appearing enhancement. Of course, neither are recommended for prophylactic use.

Crawford et al U.S. Pat. No. 1,362,398 provides for a surgical splint, using soft rubber and thus discloses the essential features of a device to strengthen the person who is wearing it. In contrast, Thorne U.S. Pat. No. 2,471,360 uses a sheath that dissolves upon insertion. The former is strictly a surgical splint and the later is, at best, for it's intended use of temporary support. Briggs U.S. Pat. No. 2,899,957 also discloses a resilient material, but is focused mainly on construction details. Again, no real consideration of a secure prophylactic device is suggested.

Dyck et al U.S. Pat. No. 4,576,156 is directed to a prophylactic devise and discloses a number of materials that were known in 1978. This patent is directed to a new material, polyurethane. Dyck identifies the primary reasons why prophylactic devices have in the past been of interest, primarily to prevent infection from venereal diseases and for the purpose of birth control. While security is of concern, mostly from the potential for leakage, nothing is said about the more current serious concern about the transmission of viruses such as those associated with AIDS.

Johnsen et al U.S. Pat. No. 5,500,469 discloses the use of SIS and SBS polymers as latexes. Johnsen forms a stable aqueous colloidal dispersion —which may not have an adequate barrier to viruses, or even male sperm. As in any latex, Johnsen is a film that can be stretched to increase it's size, and as it stretches, it becomes thinner.

When a latex is examined under a microscope of sufficient magnification, the latex film appears to be formed from a plurality of spherical shapes with spaces therebetween. One can picture a wall made of golf balls, having many spaces between the solid objects. Latexes have these holes and, thus, are not always effective in preventing very small objects from passing between the solid material through the holes. Viruses are capable of passing through a normal latex condom even when the condom maintains its appearance of integrity. A latex condom may still be water tight and even expandable by air pressure, such as if it were a balloon, and yet viruses can pass through the latex.

Finally, Wheeler et al U. S. Pat. No. 5,526,823 discloses a variety of stress softened elastomeric films that may be used as prophylactic devices such as gloves, condoms and the like. This patent recognizes the concern for the sexual transmission of AIDS and the reliance on condoms for the prevention of the same. This patent lists a large number of materials from which prophylactic and/or prosthetic devices may be made. Among these are the above mentioned Dyck et al patent. Other materials disclosed are: polyurethane, polypropylene film, polyethylene teraphthalate film, ethylene/vinyl acetate copolymer films, ultra-high molecular weight polyethylene, polyether block amides, polyester elastomers, vinyl materials and latexes. The specific intent of Wheeler et al is to stress soften whatever material is used.

None of the prior art really addresses the issue of latex film expansion and none of the inventors provide for alternative ways to obviate the deficiencies of elastomeric films such as those disclosed in the various cited prior art patents.

Accordingly, it is an object of the present invention to provide a prosthesis for the male sex organ that has an appropriate appearance and that effectively enhances that organ's size while maintaining a physical and tactile similarity to the human organ.

Another object of this invention is to provide a prophylactic device such as a condom that is more highly resistant to penetration by extremely small objects such as viruses.

Yet another object of the present invention is to provide a material that may be easily formed into a device that is both prophylactic and prosthetic, for use in conjunction with the male sex organ.

Other objects will appear hereinafter.

SUMMARY OF THE INVENTION

It has now been discovered that the above and other objects of the present invention may be accomplished in the following manner. Specifically, the present invention provides a device useful for prophylactic and prosthetic assistance for the human male sex organ.

The device comprises an elastomeric gel formed into a tubular shape generally replicating that of the human male sex organ or member. In some embodiments, the size and shape is larger than the actual sex organ of the user, and thus functions to enhance the size of the user. In other embodiments the device is simply cylindrical, much like an ordinary condom or prophylactic device, having a wall thickness that permits the wall to follow the contour of the user's body part.

The device in either embodiment is generally tubular, and is closed at one end and open at the other end. The exterior surface is formed from the elastomeric gel to simulate the color, physical properties and tactile feel of human flesh. Dyes and colorants are added to achieve the visual replication, while the gel itself, as described below, replicates the tactile feel of the human male sex organ. When wet with water soluble fluids such as lubricants or natural fluids of a female partner, the exterior has relatively low friction similar to the human skin that it replicates.

The interior of the device is hollow to provide space for insertion of the human male sex member, normally in an aroused state, into the open end. There are no belts, straps or other means for attaching the device of this invention to the user. These added paraphernalia are not needed, and thus do not detract from the natural appearance of the device. The texture of the interior surface of the elastomeric gel is sufficiently tacky or sticky, with a high coefficient of friction, so that it will adhere to the skin of the male user.

The preferred elastomeric gel is formed from a mixture of plasticizing oil and a block copolymer selected from styrene ethylene butylene styrene block (SEBS) copolymers and styrene ethylene propylene styrene (SEPS) block copolymers. Preferred are mixtures of both block copolymers in a ratio of 1:5 to 5:1, with about 1:1 being most preferred. Particularly preferred are gels formed from a mixture of 5–15% by weight of the block copolymer and 85–95% by weight of the plasticizing oil, of course with trace amounts of pigments and fillers. More preferred is 85–90% oil and 10–15% block copolymer. The gel is also sufficiently flexible to roll about its circumference from its open end to facilitate wearing and removing said device much in the same manner as conventional condoms. The general appearance may, as noted above, resemble such conventional condoms, perhaps with a more natural coloring, or it may have the physical shape, size and general visual appearance of the male sex organ.

DETAILED DESCRIPTION OF THE PREFERRED EMBODIMENT

Figure 1:
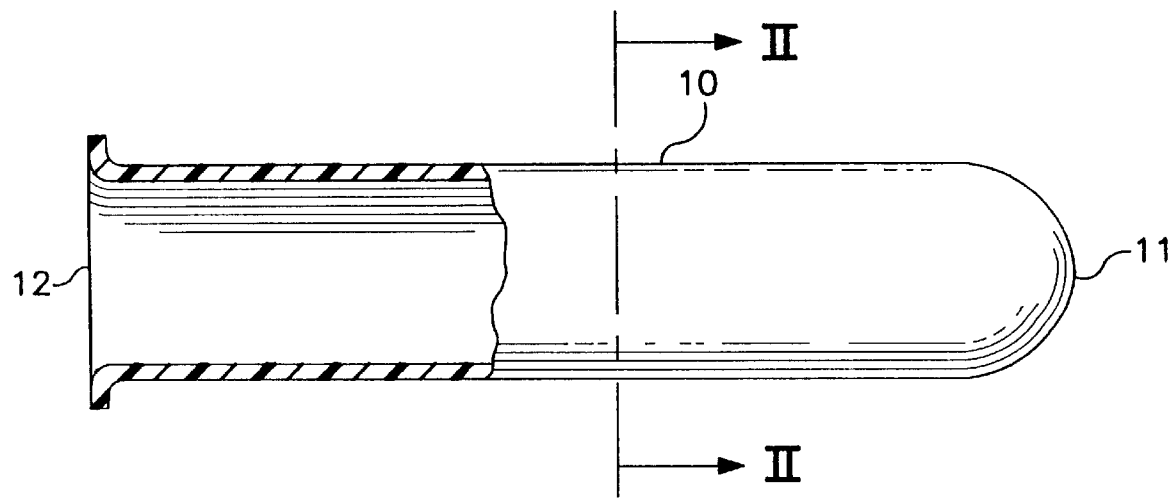
FIG. 1 is a side elevational view, partially cut away, of the present invention in one embodiment.
Figure 2:
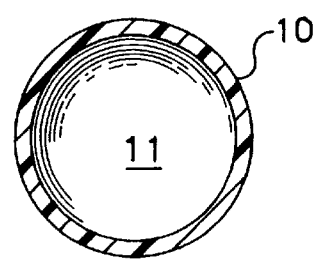
FIG. 2 is a section view of the device shown in FIG. 1, taken along line II—II.

The prosthetic and prophylactic device of the present invention is formed by molding an elastomeric gel in a predetermined shape so that it may be fitted on or worn by the male user. In order to accomplish the objects of this invention, it is important to select an elastomeric gel that closely simulates the appearance and feel of human flesh.

The device of the present invention may be molded by injection molding or cast or formed using other conventional methods of forming elastomeric gels in particular shapes. Since the device may simulate the appearance of the human body member on which it is designed to be worn, realistic modeling techniques may be employed. If the device is only to resemble a condom, or a rolled cylinder, a much simpler mold may be used. The device is an insoluble, continuous elastomeric gel formed into a tublular shape 10 closed at one end 11 and open at the other end 12 such that the gel has the appearance that simulates the color, physical properties and tactile feel of human flesh.

The elastomeric gel used to form the device of this invention is preferably formed from a mixture of plasticizing oil and a block copolymer or other elastomer that combines with oil in the same manner. One source of elastomeric gels is disclosed in a series of patents to John Chen. These include U.S. Pat. Nos. 4,369,284; 4,618,213; 5,153,254; 5,262,468; 5,334,646; and 5,336,708. These patents describe a variety of gelatinous compositions using an admixture of poly(styrene-ethylene-butylene-styrene) triblock copolymers having styrene end block to ethylene and butylene center blocks with various ratios as disclosed, plus high levels of plasticizing oils ranging from 300 to 1600 parts of oil per 100 parts of copolymer.

The Chen patent products may be generically referred to as SEBS gels. Of course, with a wide range for the oil to polymer ratio, products having many different properties are produced, depending on the specific ratio chosen. For the purposes of this invention, a gel may be produced having the general resilience and hardness of human flesh, particularly in the human male sex organ that is being duplicated for use herein. Higher molecular weight SEBS polymers, such as disclosed in Chen, are preferred.

Also preferred elastomeric gels are styrene-ethylene propylene-styrene block copolymers, called SEPS, that is highly extended with oil such as mineral oil, such that the ratio of SEPS to oil is carefully controlled to simulate the tactile feel of flesh. Preferred are SEPS polymers having a number average molecular weight of at least 150,000 to 200,000.

The SEPS is highly extended with oil such as mineral oil, so the ratio of SEPS to oil is carefully controlled to simulate the tactile feel of flesh. White mineral oil, naphthenic oils, and synthetic oils are preferred.

Other oils include petroleum paraffinic oils, petroleum naphthenic oils, synthetic polybutene oils, synthetic polypropene oils, synthetic polyterpene oils and mixtures thereof.

The most preferred gel for use with the present invention is a mixture of plasticizing oil and a block copolymer selected from styrene ethylene butylene styrene block (SEBS) copolymers and styrene ethylene propylene styrene (SEPS) block copolymers. Preferred are mixtures of both block copolymers in a ratio of 1:5 to 5:1, with about 1:1 being most preferred. Particularly preferred are gels formed from a mixture of 5–15% by weight of the block copolymer and 80–95% by weight of the plasticizing oil, of course with trace amounts of pigments and fillers. Most preferred is 85–90% oil and 10–15% block copolymer.

The elastomeric gel is often supplied as a crumb polymer for ease of mixing and processing. The amount of block copolymer used in the present invention is that amount which mixes with the oil component to provide the desired resiliency and other properties to replicate human flesh. Typically the composition will include about 5% to about 15% by weight based on the total gel weight, and preferably between about 10% and 15% elastomeric gel such as SEBS, SEPS and mixtures thereof.

The remainder of the composition is selected to give the visual and textural feeling that approximates human flesh. Preferred is to add an antioxidant. It is also desirable to accompany the tactile feel of flesh with the appearance of flesh, so that a quantity of pigment, dye or other colorants is added. Preferred color adjusting additives contain titanium dioxide and minor amounts of color pigments.

The gel may also be coated with various materials to assist in optimizing the surface characteristics, as long as the gel has the resilience and hardness that human flesh has. Obtaining the desired surface tack, in most cases, requires an additional component to adjust the 'feel' of the material. For example, talc may be applied to the surface to adjust the coefficient of friction, or petroleum jelly may be used to increase lubrication before it is inserted.

EXPERIMENT ONE

In order to demonstrate the effectiveness of the present invention, a soft pink gelatinous material was prepared. The material was prepared by:

1. forming a dry blend of SEPS and USP Mineral Oil with sufficient heat to facilitate blending.
2. adding minor amounts of a conventional antioxidant to more Mineral Oil, then heating the oil/antioxidant, followed by adding 200 grams of the blend in paragraph #1 above under constant high sheer, followed by addition of pink color pigment.
3. the resulting hot liquid formulation is cast hot into convenient slab form for later remelting.
4. transferring slabs formed in #3 above to a hot melt dispenser.
5. molds which are to be filled are first warmed with the gelatinous composition, then the mold is filled by dispensing from hot melt dispenser. The mold may be coated with Teflon® coating to facilitate release.

6. remove the product and dust with corn starch or other surface conditioner to aid in removal from mold core and adjust the tackiness or coefficient of friction to more closely simulate the intended human body part.

The resultant product is readily molded into shapes that closely simulated human flesh. The final product contained 90% oil and 10% SEPS. Other similar experiments were performed as above, with the only difference being the amount of oil in the formulation.

EXPERIMENT TWO

An extra soft tan gelatinous material was prepared to simulate human flesh. The final product contained 85% oil and 15% SEBS/SEPS in a 1:1 ratio. The material was prepared by the same method described for Experiment One. Again, the resultant product closely simulated human flesh.

EXPERIMENT THREE

An soft pink gelatinous material was prepared to simulate human flesh. The final product contained 95% oil and 5% SEBS. The material was prepared by the same method described for Experiment One. Again, the resultant product closely simulated human flesh.

Products in accordance with the present invention have been fabricated using the following technique from both materials set forth in Examples One, Two and Three.

An artificial human male sex organ is sculpted or otherwise formed and a mold is prepared in a conventional manner. One such mold comprised an outer shell having a length of approximately 9.5 inches, centered inside of which is supported an 8 inch cylindrical rod to form the inner portion of the device. Hot, melted elastomeric gel is injected into the mold in the normal manner and withdrawn. The resulting device is generally cylindrical, subject to the shape of the member that it replicates, and has a nominal diameter of 1.125 to 1.25 inches. When used, the device thus adds an increase in diameter of about 0.25 inches and about one inch in length. In this form of the invention, the device serves a size enhancer for the users.

Whether the device is formed as a simple condom shape or in a shape that simulates the body part, it is capable of being rolled about its circumference in the manner of a conventional condom. The inside of the device is left untreated, which when the preferred elastomeric gels are used, has a high enough degree of tack so that the device will not move with respect to the male sex organ on which it is fitted. The outer surface, however, is wetted or otherwise lubricated with water soluble fluids to provide a realistic coefficient of friction for inserting into a partner. The advantages of having no belts, straps or other paraphernalia to detract from the use of the device is clear.

As can be appreciated from the description of the elastomeric gels described above, the gel functions in several advantageous ways. Clearly, the size of the user is enhanced. Secondly, since the device does not move with respect to the male user's sex organ, there is less sensation of contact, thus serving as a preventative to premature climax. Some sensation is transmitted through the device, but not as much as would be without the presence of the device. Another advantage is that the device is made from a gel that is continuous, rather than like that of conventional latex rubber condoms. Even when inspected under microscopic magnification, the wall is continuous and does not have openings that would permit transmission of sperm, for example, or even smaller openings that would permit a virus to pass through the wall. Thus hygienic and health benefits are clearly obtained. The device of the present invention is washable and reusable, since the elastomeric gel does not deteriorate in the presence of water.

While particular embodiments of the present invention have been illustrated and described, it is not intended to limit the invention, except as defined by the following claims.

I claim:

1. A device useful for prophylactic and prosthetic assistance for the human male sex organ, comprising:

an insoluble, continuous elastomeric gel formed into a tubular shape generally replicating that of the human male sex organ or member, said shape being closed at one end and open at the other end thereof;

the exterior of said device having an appearance that simulates the color, physical properties and tactile feel of human flesh, and, when wet with water soluble fluids, has relatively low friction similar to the human skin that it replicates; and the interior of said device being hollow to provide space for insertion of the human male sex member in an aroused state into the open end, the texture of the interior surface being sufficiently tacky to stick to the skin of the male user.

2. The device of claim 1, wherein said elastomeric gel is formed from a mixture of plasticizing oil and a block copolymer selected from SEBS block copolymers, SEPS block copolymers and mixtures thereof.

3. The device of claim 2, wherein said elastomeric gel is formed from an admixture of (i) SEBS block copolymer and (ii) SEPS block copolymer combined in a ratio of 1:5 to 5:1.

4. The device of claim 3, wherein said ratio of said copolymers is about 1:1.

5. The device of claim 2, wherein said elastomeric gel is formed from a mixture of 5–15% by weight of said block copolymer and 85–95% by weight of said plasticizing oil, and trace amounts of pigments and fillers.

6. The device of claim 5, wherein said gel is sufficiently flexible to roll about its circumference from its open end to facilitate wearing and removing said device.

7. The device of claim 1, wherein said device is formed to have the physical appearance of the male sex organ.

8. The device of claim 1, wherein said exterior has a generally cylindrical shape such as that of conventional condoms.

9. A device useful for prophylactic and prosthetic assistance for the human male sex organ, comprising:

an insoluble, continuous elastomeric gel formed from a mixture of plasticizing oil and a block copolymer selected from styrene ethylene butylene styrene block copolymers and styrene ethylene propylene styrene block copolymers, said gel being configured in a tubular shape generally replicating that of the human male sex organ or member, said shape being closed at one end and open at the other end thereof;

the exterior of said device having an appearance that simulates the color, physical properties and tactile feel of human flesh, and, when wet with water soluble fluids, has relatively low friction similar to the human skin that it replicates; and the interior of said device being hollow to provide space for insertion of the human male sex member in an aroused state into the open end, the texture of the interior surface being sufficiently tacky to stick to the skin of the male user, said gel being sufficiently flexible to roll about its circumference from its open end to facilitate wearing and removing said device.

10. The device of claim 9, wherein said elastomeric gel is formed from a mixture of plasticizing oil and a block copolymer selected from SEBS block copolymers, SEPS block copolymers and mixtures thereof.

11. The device of claim 10, wherein said elastomeric gel is formed from an admixture of (i) SEBS block copolymer and (ii) SEPS block copolymer combined in a ratio of 1:5 to 5:1.

12. The device of claim 9, wherein said elastomeric gel is formed from a mixture of 10–15% by weight of said block copolymer and 85–90% by weight of said plasticizing oil, and trace amounts of pigments and fillers.

13. The device of claim 9, wherein said device is formed to have the physical appearance of the male sex organ.

14. The device of claim 9, wherein said exterior has a generally cylindrical shape such as that of conventional condoms.

* * * * *